July 29, 1958 E. V. GOLDSMITH ET AL Plant Pat. 1,735
VARIETY OF STRAWBERRY
Filed June 29, 1956
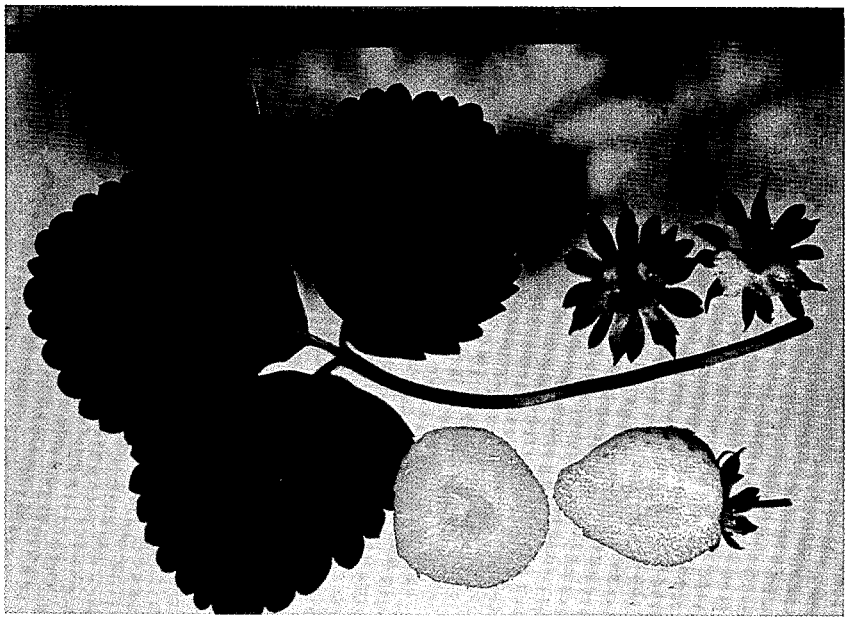
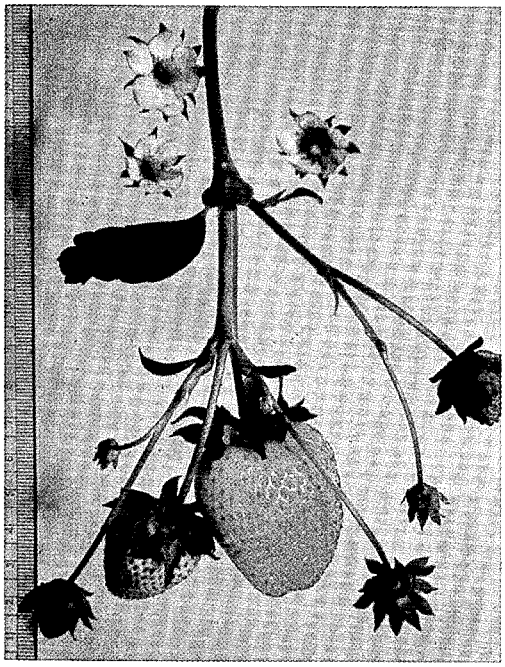
INVENTORS
HAROLD E. THOMAS and
MARGARET S. GOLDSMITH
EXECUTRIX FOR THE ESTATE OF
EARL V. GOLDSMITH
BY Hansen and Lane
THEIR ATTORNEYS United States Patent Office Plant Pat. 1,735
Patented July 29, 1958

1,735

VARIETY OF STRAWBERRY

Earl V. Goldsmith, deceased, late of Morgan Hill, Calif., by Margaret S. Goldsmith, executrix, San Jose, and Harold E. Thomas, Morgan Hill, Calif.; said Margaret S. Goldsmith assignor to The Strawberry Institute of California Application June 29, 1956, Serial No. 595,038

1 Claim. (Cl. 47—62)

The invention described herein relates to a distinctly new strawberry variety resulting from a cross of two University of California seedling selections numbered 638.45 and 469.5. The seedlings resulting from this cross were first fruited at Waterford, California. The strawberry plant embodying the present invention was selected from this group of seedlings and further asexual reproduction was carried out in the same area by rooting runner plants which originated from the mother seedlings. Further testing carried on in various parts of California during intervening seasons indicating the merit of this plant in numerous locations on properties of members of the Strawberry Institute of California resulted in its selection as a promising test variety.

In the accompanying drawing two photographic pictures are presented:

The uppermost picture shows a view of one leaf of the plant showing the color and characteristics thereof; a top plan view of the calyx bud of the fruit; a fruit side view of the calyx from which the fruit has been removed; a transverse section through the fruit; and a longitudinal section through the fruit and calyx.

The lowermost picture shows a side view of an inflorescence or blossom and also a fruit bearing system.

The plant is a small, open crowned type with leaves and petioles smaller than those of the Shasta variety. The Shasta is a variety introduced in 1945 by applicants herein for the University of California. The Shasta is a standard variety grown in California more than in any other State. The Shasta variety although not patented is known to the Bureau of Plant Industry Agricultural Research Center at Beltsville, Maryland. The plant of the present application is sensitive to any adverse condition, and will produce a characteristic purple coloring when it is subjected to excessive heat, lack of water, or nutrients, or injury from disease or insects. When growing normally its leaves have a deep dark green color and are slightly wrinkled. In the nursery the plant is a very good runner maker.

The fruit of the present invention is larger than the Shasta variety and has a higher surface gloss. The berries are mostly long wedge in shape and this characteristic, along with its large size and glossy appearance, especially during the first growing year, makes it an excellent fresh market variety for both local and long distance shipment. The fruit is borne on inflorescences of medium length with the pedicel of the primary berry and the secondary fruiting stems branching from a common axil on the main fruiting stem as illustrated in Fig. 6. This is in contrast to the inflorescences of the Shasta variety which generally produces its secondaries from two separate axils on the main fruiting stem with the pedicel of the primary berry coming from one of the axils. The hair on the pedicel below the flower lays close to the pedicel and does not make a large angle as does Shasta. In contrast with Shasta the calyx does not produce two rows of sepals and the latter are narrower and not as serrated at their apex. The moderately red flesh gives an acceptable color to the sliced frozen fruit. It is rated as a good berry for freezing purposes.

The fruiting season for this variety is normally about the same as for the Shasta variety with the exception that the start of production in the spring is a little later. Production usually starts during the middle or latter part of April in the interior and warmer coastal valleys of California and with ups and downs in production, the plant of the present invention bears until cold weather or fall rains. In southern California production starts much earlier in the year and in cool coastal areas somewhat later. If plants are set out in late fall or early winter in the southern or coastal areas a good crop is often harvested the first year. In this respect the variety will usually bear much heavier than the Shasta variety.

In comparison to the Shasta variety the dessert quality of this new variety is about equal, with a mild sub-acid flavor. The berry of the present invention has no particular aroma.

The new variety of this invention is susceptible to Verticillium wilt and the red stele disease. It is affected by mildew, especially on the foliage. It is also susceptible to two spotted mite and cyclamen mite. The longevity of the present variety is sometimes short indicating susceptibility to virus.

The varietal characteristics that are described below in detail were observed in second year testing beds during August, September and October at Watsonville, California, which is a cool coastal area near the Pacific Ocean. The color terminology is in accordance with Ridgeways Color Standards and Nomenclature (1912 edition).

Plant: Small to medium size, open crown, moderate to low vigor and longevity, and root system of medium size and vigor.

Leaves: Medium size, central leaflet diameter 5 to 8.5 cm. Upperside of main vein of central leaflet of vigorously growing leaves is noticeably wide at the base, 1 to 2 mm. Leaflets—flat to wavy of surface with some cupping upward; mildly rugose giving a slight wrinkled appearance. Leaves show purple coloring when plant is subjected to any adverse condition such as severe hot weather; lack of nutrients or water; or injury from disease or insects. The outline of the serrations on the margins of the leaflets is ovate with an acute apex. Color—upperside—Dark Cress Green, Plate XXXI; lowerside—Bryce Green, Plate XVII. Petiole—medium long, mostly 13 to 20 cm.; petiolule of central leaflet mostly 6 to 8 mm.; color—Lettuce Green, Plate V.

Runners: Vigorous, medium to long internodes, many runners and runner plants produced the first year and a few the second in fruiting beds. Nursery production of plants is high.

Inflorescence: Medium long, mostly 15 to 20 cm. with a short main fruit stem. In most of the inflorescences the pedicel of the primary berry and the peduncles of the secondary berries originate from a common axil on the main fruiting stem. The hair on the tertiary pedicel 20 mm. below the flowers lays against and parallel with the pedicel. Some bloom is visible above the foliage.

Fruit: Consistently large, with length of primaries or well developed secondaries, mostly 40 to 45 mm., width mostly 30 to 50 mm. Most berries are long wedge in form, but may vary between a long conical and a long wedge. The shoulders of most berries are large and rounded giving an outline like the upper half of a heart. Some shoulders may taper downward, however, but no berries are necked. Surface—uniformly glossy; skin reasonably firm. Color—Carmine Red, Plate I. Flesh—firm, juicy; color—Nopal Red, Plate I. Seeds—medium in size, held even to slightly above the surface, evenly spaced, very few non-fertile, medium in number; color—Apricot Yellow, Plate IV.

Calyx: Large with diameter 30 to 40 mm. average of 36 mm. Sepals—long, 10 to 15 mm., and narrow with linear to lanceolate outline; held free from each other and narrowing at the point where they join the base of the calyx; not formed in overlapping rows; averaging 10 to 12 in number. Some serrations at the apex of the sepals on large flowers, but none are present on the sepals of small flowers. The calyx may be either clasping or free of the fruit.

We claim:

A new and distinct variety of strawberry plant, substantially as herein described, characterized by its small size and moderate vigor; by its large glossy wedge shaped fruit which are produced over a long fruiting season; by its ability to produce a large crop during the first growing year; and its good carrying quality when shipped to markets out of State.

No references cited.